United States Patent [19]

Nugent

[11] Patent Number: 4,620,549

[45] Date of Patent: Nov. 4, 1986

[54] BLOOD COLLECTION ASSEMBLY

[75] Inventor: Edward L. Nugent, Caldwell, N.J.

[73] Assignee: Becton, Dickinson and Company, Franklin Lakes, N.J.

[21] Appl. No.: 695,121

[22] Filed: Jan. 25, 1985

[51] Int. Cl.[4] .......... A61B 5/00

[52] U.S. Cl. .......... 128/763; 604/264

[58] Field of Search .......... 128/763–767, 128/770; 215/211, 306; 604/192, 199, 263, 264

[56] References Cited

U.S. PATENT DOCUMENTS

| | | | |
|---|---|---|---|
| 2,705,955 | 4/1955 | Nesset et al. | 215/306 |
| 2,941,531 | 6/1960 | Stevens | 128/764 |
| 3,108,591 | 10/1963 | Kelbes | 128/764 |
| 3,381,813 | 5/1968 | Coanda et al. | 604/192 |
| 3,848,780 | 11/1974 | Stull | 215/211 |
| 3,908,638 | 9/1975 | Porcher et al. | 128/763 |
| 4,024,857 | 5/1977 | Blecher et al. | 128/2 F |
| 4,215,700 | 8/1980 | Crouther et al. | 128/763 |
| 4,250,893 | 2/1981 | White | 128/765 |
| 4,280,631 | 7/1981 | Lohrman | 215/216 |
| 4,397,318 | 8/1983 | Burns | 128/763 |
| 4,411,163 | 10/1983 | White | 73/864.02 |
| 4,534,763 | 8/1985 | Gettig et al. | 128/763 |
| 4,548,332 | 10/1985 | Neat | 215/306 |

*Primary Examiner*—Edward M. Coven
*Assistant Examiner*—Max F. Hindenburg
*Attorney, Agent, or Firm*—Robert P. Grindle

[57] ABSTRACT

A blood microcollection container and associated collection assembly is provided for engaging a puncture wound and rapidly receiving blood from the wound. The assembly incorporates a scoop arrangement for engaging the blood source, and for directing in a rapid and efficient manner the blood to a collection chamber. A two-position cap is provided for sealing the scoop collector of the assembly prior to use, and for permanently locking to the collector after use to prevent exposure to the blood sample by the person handling the blood sample, or contamination of the blood sample from outside sources.

14 Claims, 4 Drawing Figures

BLOOD COLLECTION ASSEMBLY

BACKGROUND AND STATEMENT OF THE INVENTION

This invention relates to a blood collection assembly incorporating a microcollection container. The invention is an improvement over the collection assembly described and claimed in U.S. Pat. No. 4,397,318, issued Aug. 9, 1983, which is hereby incorporated by reference in its entirety. Reference should be made to that patent for background information concerning the teachings of the invention here. The earlier patent involved the use of a scoop collector for connection to a blood microcollection container for engaging a puncture wound to obtain a blood sample from an individual for subsequent examination of that sample for the determination of the presence or absence of some disease or other problem in a patient. The scoop-type blood collection device provides a substantially larger engaging surface for engaging the puncture for collecting the blood, and a substantially larger transfer surface for rapidly transferring the blood from the collector into the microcollection container. Because of the relatively large engaging surface for engaging the puncture wound, the arrangement does not require a precise positioning of the scoop engaging surface in order to initiate and rapidly transfer a quantity of blood to the microcollection container.

As will be appreciated by practitioners-in-the-art, recent advancements in analytical instrumentation have made it possible to carry out a variety of hematological or chemical diagnostic procedures on very small quantities of blood. Because of this, a patient's finger or earlobe may be punctured and a very small quantity of blood rapidly collected into a microcollection container for such testing. Such arrangements obviate the need to withdraw venous blood from patients. However, such collection arrangements must be such that the blood is rapidly collected prior to any coagulation thereof. In the past, prior to the scoop collector disclosed in the above-noted U.S. Pat. No. 4,397,318, a cap or top arrangement was configured to fit on the top of a microcollection container with the top having an integral capillary tube for engaging the puncture and transferring blood to the cntainer. However, with such an arrangement, the tip of the capillary tube had to be arranged precisely adjacent the puncture would and the entire apparatus had to be so positioned that the blood flow along the bottom surface of the tubular microcollection container moved continuously in order to engage the surface of the container. Otherwise, if a precise positioning was not carried out, capillary action was not initiated or slowed with subsequent clotting. Representative such collectors are taught in U.S. Pat. No. 4,024,857, issued May 24, 1977.

One problem with the scoop collector taught and claimed in U.S. Pat. No. 4,397,318, although the arrangement taught herein is highly efficient for the rapid collection of a blood sample into a microcollection container, is the fact that the assembly for making the collection must be distributed with the microcollection container or tube having a separate cap for entrainment of additions, for example. Therefore, the technician must remove the cap, and place on the container the scoop collector prior to making a collection of a blood sample. Subsequent to this collection, moreover, the scoop collector must then be removed, and the cap replaced on the container for delivery of the specimen to a lab for investigation of the sample. Such removal and replacement of parts on the top of the blood microcollection container is cumbersome, as one will understand, particularly if the technician is, for example, attempting to take a blood sample from a screaming, wiggly baby. Moreover, the technician or nurse or doctor may become exposed to the blood sample during this transfer procedure in removing the blood collection scoop arrangeent and replacing the cap on the blood microcollection container.

With this invention, by contrast, a scoop arrangement is incorporated into a blood microcollection assembly in such a way that the scoop collector does not have to be removed until such time as the technician in the laboratory wishes to obtain access to the sample in the blood microcollection container. This is achieved by the use of a cap which is a two-position cap. That is, the assembly is distributed to potential users with the cap in place over the scoop collector on the top of the blood microcollection container.

When the nurse or doctor wishes to take a blood sample, the cap is removed and the front end of the scoop collector is placed adacent the wound for collection of blood. Once the blood sample has been taken, the cap is again placed over the scoop collector without any removal of the scoop collector, as in the past. Then, the technician merely has to press-fit the cap down over the scoop collector. This press-fit movement has the effect of permanently locking the cap onto the scoop collector. Therefore, access to the blood sample in the container cannot be obtained unless the cap and the scoop collector arrangement are removed simultaneously. For this reason, no one can be exposed to any blood left in or around the scoop collector arrangement after the sample has been taken, and until such time as the sample is to be obtained from the microcollection tube at the lab.

As practitioners-in-the-art will understand, this arrangement reduces the amount of fumbling and movements necessary during the course of taking a blood sample while at the same time reducing the possibility of contamination to the nurse or anyone else present during the taking of the sample.

Other objects and advantages of this invention will be apparent from the following description, the accompanying drawings and the appended claims.

DETAILED DESCRIPTION OF THE INVENTION

Figure 1:
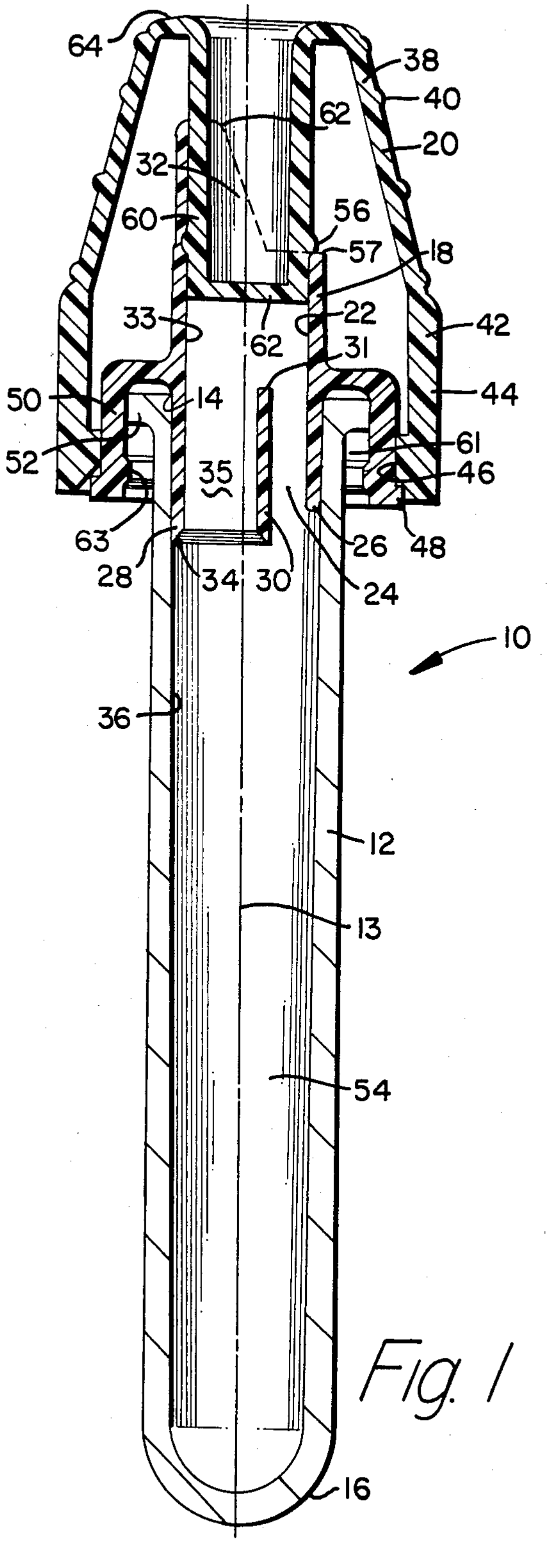
FIG. 1 is a side elevational view in section of the blood microcollection assembly of the invention including a sample collection container having disposed on the top thereof a scoop collector and cap.

Referring to the drawings in which like reference characters refer to like parts throughout the several views thereof, FIG. 1 illustrates the invention as employed with a scoop collector similar to that taught in the above-noted United States Patent utilizing a vane or septum separating, in the blood collector on the top of the blood collector container, a blood collection passage from an air vent passage.

In FIG. 1, the device 10 includes a blood microcollection container in the form of a tube 12 having a closed end 16 and an open end 14. The tube is a conventional blood microcollection tube and may be comprised of such materials as polyethylene, polypropylene or glass. Appropriately, tube 12 will be transparent or translucent to enable the nurse to know the quantity of blood collected. For the purpose of understanding the invention here and its position in use, reference is made to FIG. 5C in U.S. Pat. No. 4,397,318. That is, the top of the device shown in the Figures is the front end, and the bottom is the left side as shown in the figures because the left side will be held so that it is the bottom of the device in use.

Positioned on the top flange 52 of tube 12 is a blood collector 18 having a scoop arrangement 32 extending forwardly thereof. The collector assembly 18 is generally tubular in cross section with a central bore 22 passing therethrough. The scoop collector 18 of the invention here is diffrent from that taught and claimed in U.S. Pat. No. 4,397,318 in that the front end edge 31 of the vane or septum 30 does not extend forwardly to form the upper edge of the scoop 32. The reason for this shorter vane 30 will be described in further detail below.

The collector 18 includes an annular integral skirt 50, as shown in FIG. 1, which is spaced from the lower 28 and upper 26 walls forming the central bore 22 of collector 18. This spacing allows for an annular space 61 for receiving in press-fit engagement the annular flange 52 surrounding the open end 14 of tube 12. The skirt 50 includes an integral internal abutment 63 which cooperates with flange 52 for maintaining collector 18 on the top of tube 12. Annular skirt 50 also includes an annular outer abutment 48 which cooerates with cap 20 for holding cap 20 locked on collector 1 as will be described below.

Referring further to FIG. 1, cap 20 includes an annular lower skirt 42, with an upper tapered portion 38 integral therewith. When cap 20 is in place as shown in FIG. 1, the wall of the annular upper portion converges from skirt 42 toward the axis 13 of the assembly shown. The outer surface of the lower skirt portion 42 of cap 20 includes a plurality of spaced ribs 44, which provide for a better grip on cap 20, when it is to be removed from the assembly, as shown. The upper tapered portion 38 also includes a plurality of annular ridges 40 which also serve to provide a gripping surface to the cap assembly 20.

The upper tapered portion 38 of cap 20 ends in a tip 64 which connects to a central tubular internal well 60 of cap 20. Well 60, as shown in FIG. 1, serves to fit internally in bore 22 of collector 18. Well 60 includes an annular abutment 56 which cooperates with the front edge 57 of upper wall 26 of collector 18 in the position of cap 20 in FIG. 1. In this connection, the term "upper" as used herein is a designation for the right-hand portion of collector 18. The term "upper" as mentioned above is used to designate the upper side of collector 18 when the assembly is in use. That is, the air vent passage 24 will be positioned upwardly, while blood collection passage 35 will be positioned downwardly in the partially horizontal position of the collector assembly during collection of a blood sample, much in the same manner as the positioning shown in the above noted U.S. Pat. No. 4,397,318.

As can be seen in FIG. 1, skirt 42 of cap 20 includes an integral inner abutment 46. Abutment 46, as shown in FIG. 1, cooperates with abutment 48 on collector 1 for engaging the collector 18 and capping the assembly prior to use. That is, the abutment 48 serves as a stop for the abutment 46 with the latter being in press-fit engagement with the outer annular surface of skirt 50 of collector 18.

Thus, a technician or nurse, wishing to collect a blood sample in the assembly 10 of FIG. 1, receives the assembly with the parts thereof in the position shown in FIG. 1. The technician removes cap 20 from collector 18, makes a skin puncture and places the front edge 62 of scoop collector 32 adjacent the puncture. Blood flows along surface 33 of bore 22 in collector 18, and passes from the rear edge 34 of that surface into and along the surface 36 of tube 12 to be collected in chamber 54 thereof. Once a proper quantity of a blood sample has been collected in chamber 54, the technician removes the front edge 62 of collector 32 from the wound and places cap 20 on colelctor 18 which in turn is still in place on tube 12. When the technician replaces cap 20, the cap is press-fit onto collector 18 to the degree wherein the annular abutment 46 on skirt 42 of cap 20 rides over the abutment 48 of collector 18 to the position shown in FIG. 2.

Thus, the abutment 46 slides down over abutment 48 and locks the cap 20 onto the collector 18. With this arrangement therefor, the collector 18 is completely covered and cannot be exposed to anyone. The entire assembly is conveyed to a lab for proper handling of a blood sample contained in chamber 54. At that time, the clinician in the lab may remove cap 20 for obtaining access to the sample contained in chamber 54. When this happens, the cap 20 automatically removes the collector assembly 18, as well, so that the entire combination of cap 20-collector 18 may be disposed of and any contaminated sample contained in collector 20 is removed from exposure to anyone handling the sample other than the appropriate handling which takes place in a clinical laboratory.

Figure 2:
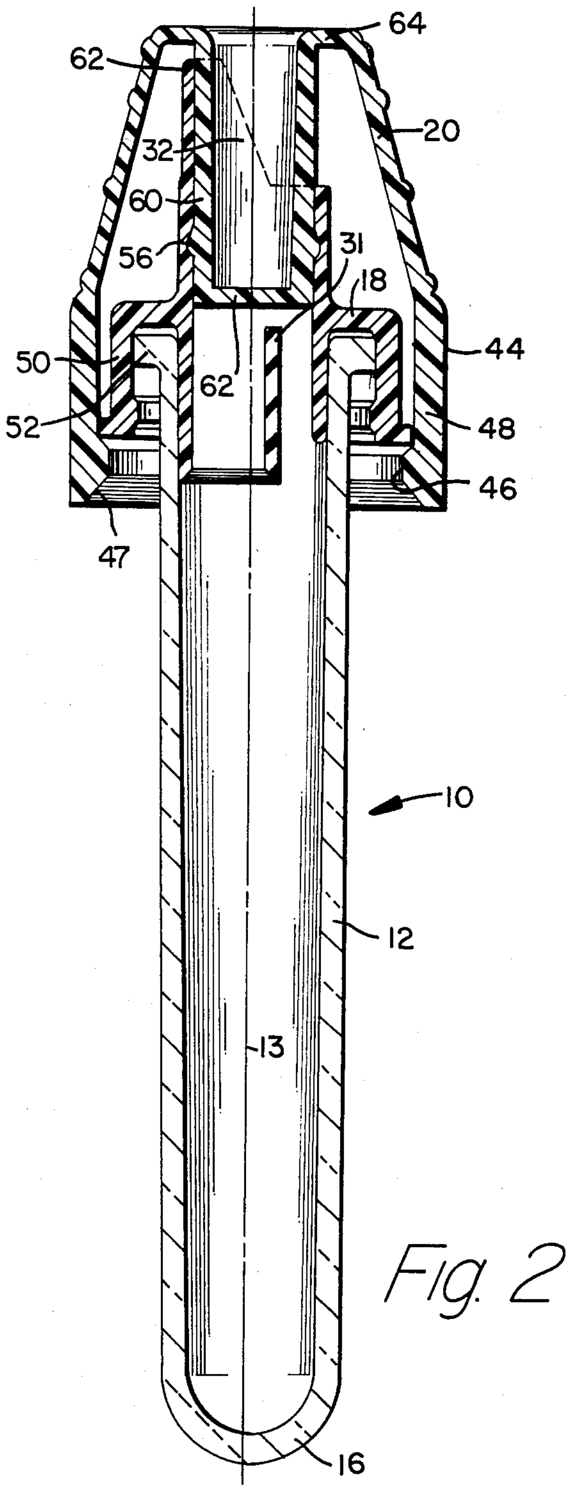
FIG. 2 is a side elevational view of the assembly of FIG. 1 in the position after the taking of a blood sample wherein the cap has been moved to its locking position over the collector assembly fitted on top of the blood collection tube.

It should be noted here that in the locked position shown in FIG. 2, the annular integral well 60 of cap 20 moves into the bore 22 of collector 18 to a point immediately adjacent the front end 31 of septum or vein 30 for effectively sealing off the bore 22 of collector 18. In this connection, the annular abutment 56 on the outer surface of the annular integral internal well 60 of cap 20 is press-fit against the wall of bore 22 for a positive sealing engagement therewith. It should be noted further that abutment 46 on annular skirt 42 of cap 20 includes a tapered surface 47 for ease of movement of cap 20 into its locked position as shown in FIG. 2. That is, the tapered surface 47 has the effect of camming the abutment 46 outwardly over the abutment 48 for cooperating locking engagement therewith.

Figure 3:
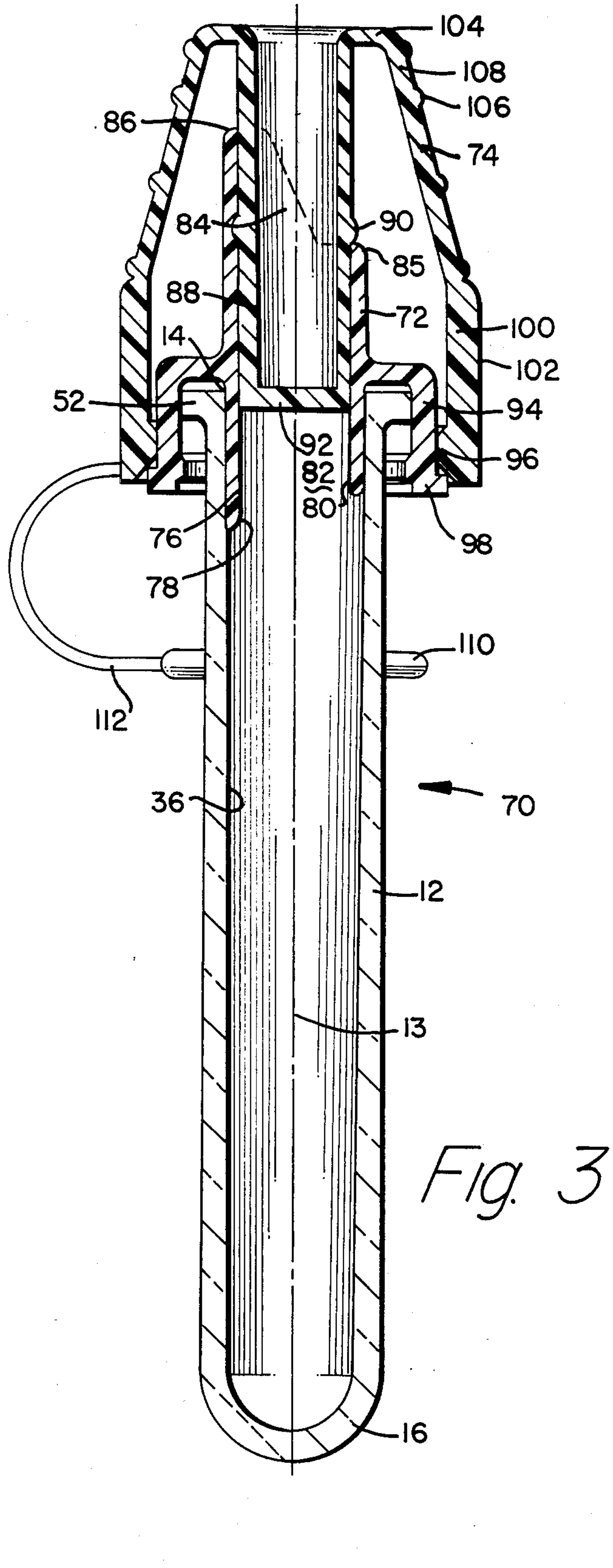
FIG. 3 is a side elevational view in section of a further embodiment of blood collection assembly illustrating the invention.
Figure 4:
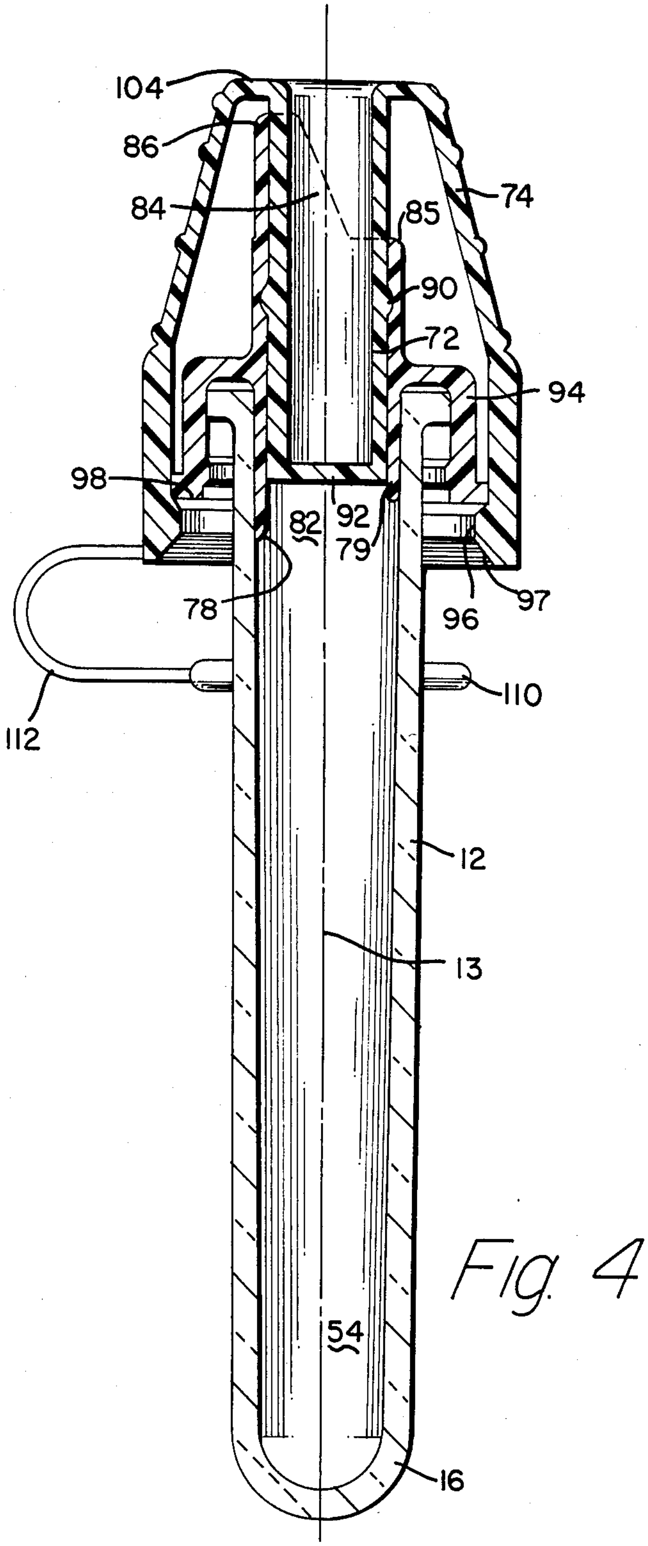
FIG. 4 is a side elevational view in section of the assembly of FIG. 3 with the cap positioned in its final locking position on the scoop collector of the assembly of the invention.

A further embodiment of blood collection assembly is shown in FIG. 3. This collection assembly is similar to that shown and described in the FIGS. 1 and 2 embodiment. However, in this embodiment, the blood collector 72 does not include any centrally positioned vane or septum 30 as shown in the FIG. 1 embodiment. Thus, the collector 72 includes a central bore 80 defining a passage 82 through which a blood sample passes. Thus, when blood is taken by scoop 84 of collector 72, the front edge 86 thereof engages the wound for receiving the blood which passes along the lower wall 76 of bore 80 and leaves the end 78 thereof where it engages the internal wall 36 of the collector tube 12. In this embodiment, the internal tubular well 88 of cap 74 is longer. Therefore, the bottom 92 of well 88 passes further into the passage 82 of collector 72, as shown in FIGS. 3 and 4. In the position of the assembly as shown in FIG. 4, the wall 92 extends substantially all the way into and fills up the passage 82 of bore 80.

The remaining parts in this embodiment are substantially the same as that in the FIGS. 1 and 2 embodiment. That is, collector 72 includes an annular integral skirt 94 with an annular outer abutment 98 which cooperates with the annular inner abutment 96 of skirt 100 of cap 74. Cap 74 is in the same form as cap 20 of FIG. 1 in that it includes an annular lower skirt portion 100 with spaced ribs 102 thereon, and tapered front end wall 108 ending in the front end edge 104. Tapered wall 108 includea a plurality of spaced annular abutment ridges 106 which serve together with the ridges 102 to provide gripping surfacea on the outer surface of cap 74 making it easier to grip to remove the entire collector-cap assembly so that the clinician in the laboratory can obtain a sample.

The cap 74, in the same manner as cap 20, has a two-position arrangement with a final locking position as shown in FIG. 4, achieved after passage of the tapered surface 97 over abutment 98 in a camming action. The annular internal well 88 of cap 74 includes an annular abutment 90 which cooperates with the front edge 85 of the upper wall portion of collector 72 in the position shown in the intially capped position of the cap 74 shown in FIG. 3. This annular abutment wedges into the bore 80 of collector 72, as shown in the final locked position of cap 74 in FIG. 4. It should be understood, in this connection, that annular abutment 90 may be positioned at other locations along the length of well 88. Either embodiment of the invention here may include an integral strap 112 on cap 74 which strap 112 is attached to a ring 110 for attaching the cap to tube 12 to prevent loss or misplacement thereof. A thumb "roll" or flange 200 may be incorporated in either embodiment of the invention here to facilitate removal of the assembly from tube 12 by the use of the thumb pushing up on flange 200.

Preferably, the assembly of the invention will be comprised of a clear or translucent molded thermoplastic such as polyethylene, for example. Other materials which may be used, as will be appreciated by practitioners-in-the-art, include various thermoplastics such as polypropylene and polyvinylchloride. The cap may be comprised of Alathon 20-6064, a polyethylene formulation of DuPont, for example. Preferably, the microcollection container itself is comprised of a clear or translucent thermoplastic material, such as polypropylene, which has been properly treated to provide a hydrophillic internal surface for enhancing the flow of blood introduced therein. Additionally, the caps may be color coded to designate acceptable and practical standards in the clinical environment, such as, for example, lavender to designate ethylenediamine tetraacetic acid for a test specimen of whole blood for hemtologies, or green for heparin in plasma specimens for chemistry.

Whereas, as discussed above, a specific embodiment of microcollection container has been shown to be used in the assembly of the invention, it should be understood that it is within the purview of this invention that other forms of microcollection containers may be used configured with different cooperating locking arrangements with the associated collection assembly and cap of the invention. That is, while the invention here teaches a press-fit engagement with the container top relative to the collector, it is within the purview of the invention that a cooperating screw arrangement could be utilized. The point is, that the collector itself cannot be removed without the cap covering it to protect the user from contamination from the time the sample is collected until such time as the lab technician removes the cap for otaining the sample contained in the container.

While the forms of apparatus herein described constitute preferred embodients of the invention, it is to be understood that the invention is not limited to these precise forms of apparatus, and that changes may be made therein without departing from the scope of the invention which is defined in the appended claims.

What is claimed is:

1. A blood collection assembly characterized by
(a) a tube-shaped container;
(b) said container having a closed end and an open end;
(c) a blood collector mounted on said open end, said collector including
 (1) a substantially tubular collector body having a tubular flow passage therethrough;
 (2) said body extending from a puncture wound engaging front end surface to a blood discharge rear end surface;
 (3) means on said body for attaching said body to said open end of said container;
 (4) vent means in said body for air displacement therethrough;
 (5) said front end surface being tapered and having a large circumferential extent;
(d) a removable cap connected to said container for mounting on said blood collector for closing the front end thereof;
(e) two-position cooperating locking means on said blood collector and said cap for removably holding said cap on said collector in a first position and for permanently locking said cap on said collector in a second position; and
(f) said two-position cooperating locking means including
 (1) a first annular abutment on said blood collector body, said first annular abutment extending outwardly from said body;
 (2) a second annular abutment on said cap, said second annular abutment extending inwardly from said cap; and
 (3) a tapered surface on said second annular abutment for camming said second abutment over said first abutment into said permanent locking second position of said cap on said collector.

2. The assembly of claim 1, further characterized by
(a) a vane positioned in said tubular flow passage, said vane dividing said tubular flow passage into a blood flow passage and said vent means.

3. The assembly of claim 1, further characterized by (a) said cap including an integral centrally positioned well coaxial with the axis of said cap; and (b) said well extending into said tubular flow passage of said collector.

4. The assembly of claim 1, further characterized by said means for attaching including (a) a tubular skirt on said collector and integral therewith; and (b) said skirt being coaxial with said tubular flow passage and spaced therefrom;

(c) whereby the annular open end of said container is received in press-fit engagement in said space between said collector body and the skirt thereof.

5. The Assembly of claim 4, further characterized by (a) a first annular abutment adjacent the lower end edge of said tubular skirt and integral therewith;

(b) said first annular abutment extending outwardly from the axis of said skirt;

(c) a second annular abutment adjacent the lower end edge of said cap and integral therewith;

(d) said second annular abutment extending inwardly from said cap toward the axis thereof; and (e) a tapered surface on said second annular abutment for camming said second abutment over said first abutment into said permanent second locking position of said cap on said collector.

6. The assembly of claim 1, further characterized by (a) a plurality of spaced ribs on the outer surface of said cap for providing a gripping surface thereon.

7. The assembly of claim 1, further characterized by (a) an integral strap connected to said cap;

(b) a ring on the end of said strap opposite said cap; and (c) said ring for surrounding said tubeshaped container for preventing loss of said cap.

8. A blood collector and cap assembly for a microcollection container, characterized by (a) a liquid collector for mounting on the open end of a microcollection container, said collector including (1) a substantially tubular collector body having a flow passage therethrough;

(2) said body extending from a puncture wound engaging front end surface to a blood discharge rear end surface;

(3) means on said body for the attachment thereof to a microcollection container;

(4) vent means in said body for air displacement therethrough;

(5) said front end surface being tapered and having a larghe circumferential extent;

(b) a removable cap for mounting on said collector body sealingly closing the front end thereof;

(c) two-position cooperating locking means on said collector body and said cap for removably holding said cap on said collector in a first position, and for permanently locking said cap on said collector in a second position and (d) said two-position cooperating locking means including (1) a first annular abutment on said blood collector body, said first annular abutment extending outwardly from said body;

(2) a second annular abutment on said cap, said second annular abutment extending inwardly from said cap; and (3) a tapered surface on said second annular abutment for camming said second abutment over said first abutment into said permanent locking second position of said cap on said collector.

9. The assembly of claim 8, further characterized by (a) a vane positioned in said flow passage of said collector, said vane dividing said flow passage into a liquid flow passage and said vent means.

10. The assembly of claim 8, further characterized by (a) said cap including an integral centrally positioned well coaxial with the axis of said cap; and (b) said well extending into said tubular flow passage of said collector.

11. The assembly of claim 8, further characterized by said means for attaching including (a) a tubular skirt on said collector and integral therewith; and (b) said skirt being coaxial with said tubular flow passage and spaced therefrom;

(c) whereby the annular open end of said container is received in press-fit engagement in said space between said collector body and the skirt thereof.

12. The assembly of claim 11, further characterized by (a) a first annular abutment adjacent the lower end edge of said tubular skirt and integral therewith;

(b) said first annular abutment extending outwardly from the axis thereof;

(c) a second annular abutment adjacent the lower end edge of said cap and integral therewith;

(d) said second annular abutment extending inwardly from said cap toward the axis thereof; and (e) a tapered surface on said second annular abutment for camming said second abutment over said first abutment into said permanent second locking position of said cap on said collector.

13. The assembly of claim 8, further characterized by (a) a plurality of spaced ribs on the outer surface of said cap for providing a gripping surface thereon.

14. The assembly of claim 8, further characterized by (a) an integral strap connected to said cap;

(b) a ring on the end of said strap opposite said cap; and (c) said ring for surrounding a microcollection container used with said assembly for preventing loss of said cap.

* * * * *